United States Patent [19]
Williams et al.

[11] Patent Number: 5,985,913
[45] Date of Patent: Nov. 16, 1999

[54] TETRACYCLIC COMPOUNDS FOR ENHANCING BIOSYNTHESIS OF ERYTHROPOIETIN, COMPOSITIONS CONTAINING SAME, AND METHODS OF USE THEREOF

[75] Inventors: Jonathan Gareth Williams, Nuneaton, United Kingdom; David R. Houck, Chapel Hill, N.C.; David Edward Smith, SeaCliff, N.Y.; Daniel Lee Rathbone, Earlsdon, United Kingdom; David Charles Billington, West Midlands, United Kingdom; Bernard T. Golding, Newcastle Upon Tyne, United Kingdom; Eric W. Collington, Knebworth, United Kingdom; John Kitchin, Middlesex, United Kingdom; Nicholas Rich, Birmingham, United Kingdom

[73] Assignee: OSI Pharmaceuticals, Inc., Uniondale, N.Y.

[21] Appl. No.: 09/069,693

[22] Filed: Apr. 29, 1998

Related U.S. Application Data

[63] Continuation-in-part of application No. 08/978,346, Nov. 26, 1997, Pat. No. 5,882,436
[60] Provisional application No. 60/032,268, Nov. 29, 1996.

[51] Int. Cl.⁶ ........................ A61K 31/35; A61K 31/365; C07D 311/78
[52] U.S. Cl. .......................... 514/453; 549/275; 549/279
[58] Field of Search ............................. 514/453; 549/275, 549/279

[56] References Cited

U.S. PATENT DOCUMENTS 5,107,032  4/1992  Erb et al. ................................ 568/435

OTHER PUBLICATIONS

Omar Farooq (1994) "Oxidation of Aromatic 1,2–Dimethanols by Activated Dimethyl Sulfoxide," *Synthesis*, pp. 1035–1036 (Exhibit 3).

Whitehouse M. W. and Leader J. E. (1966) "Biochemical Properties of Anti–Inflammatory Drugs–IX," *Biochemical Pharmacology* vol. 16, pp. 537–551 (Exhibit 4).

*Primary Examiner*—Johann Richter
*Assistant Examiner*—Taofiq A. Solola
*Attorney, Agent, or Firm*—John P. White; Cooper & Dunham LLP

[57] ABSTRACT

The present invention provides a compound in substantially pure form having the structure:

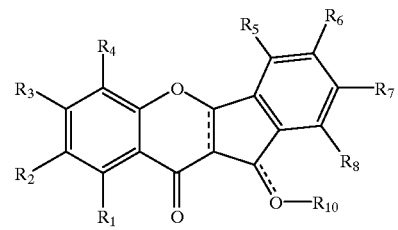

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl, wherein $R_{10}$ is $COC_{1-5}$ alkyl; or wherein any two consecutive R groups may be members of a $C_5$–$C_6$ membered ring, and wherein the intracyclic-dashed line represents a covalent bond which may be present or absent, with the proviso that when $R_{10}$ is present, the exocyclic-covalent bond is absent, and when $R_{10}$ is absent, the exocyclic-covalent bond is present, and with the proviso that when $R_{10}$ is absent, $R_1$, $R_2$, $R_3$, $R_4$, $R_5$, $R_6$, $R_7$, and $R_8$ cannot all be hydrogen and when $R_{10}$ is absent, $R_5$, $R_6$, $R_7$, and $R_8$ cannot all be hydrogen when either $R_1$, $R_2$, $R_3$, or $R_4$ is hydroxy, or R2 is carboethoxy. The present invention further provides a composition comprising the compound described above in an amount effective to modulate cellular expression of a mammalian gene encoding erythropoietin and a carrier.

28 Claims, 1 Drawing Sheet

TETRACYCLIC COMPOUNDS FOR ENHANCING BIOSYNTHESIS OF ERYTHROPOIETIN, COMPOSITIONS CONTAINING SAME, AND METHODS OF USE THEREOF

This application is a continuation-in-part of U.S. Ser. No. 08/978,346, filed Nov. 26, 1997 now U.S. Pat. No. 5,882,436 which claims the priority of U.S. Provisional application Ser. No. 60/032,268, filed Nov. 29, 1996, the contents of each of which are hereby incorporated by reference into the present application.

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Erythropoietin (Epo) is a hematopoietic growth factor which stimulates the differentiation and supports the survival of cells of erythroid lineage. During fetal development the liver serves as the primary source of Epo. Shortly before birth, production of Epo in the liver decreases and the kidney becomes the primary source. In both tissues, Epo transcription is subject to physiological regulation at the level of gene transcription in response to hypoxia, a process which can be mimicked by cobalt chloride ($CoCl_2$) in vitro and in vivo. Mechanistic studies have identified a cobalt-hypoxia, response heme protein which is capable of directly stimulating the transcription of Epo in vitro.

Injectable recombinant erythropoietin (Epo) is used currently as the therapy of choice for the treatment of anemia due to chronic renal failure. For example, Epo has been approved for the treatment of anemia associated with chemotherapy, as well as being developed for the anemia that develops as a consequence of AIDS, anemia due to prematurity and for autologous blood donation. Epo has even been suggested as a general use agent in pre-operative elective surgery. However, its extensive use could be limited by high production costs and lack of oral bioavailability. Therefore, small molecules that induce endogenous Epo will have significant utility for effective treatment of the above disorders.

SUMMARY OF THE INVENTION

The present invention provides a compound in substantially pure form having the structure:

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl, wherein $R_{10}$ is hydrogen or $COC_{1-5}$ alkyl; or wherein any two consecutive R groups may be members of a $C_5-C_6$ membered ring, and wherein the intracyclic-dashed line represents a covalent bond which may be present or absent, with the proviso that when $R_{10}$ is present, the exocyclic-covalent bond is absent, and when $R_{10}$ is absent, the exocyclic-covalent bond is present, and with the proviso that when $R_{10}$ is absent, $R_1$, $R_2$, $R_3$, $R_4$, $R_5$, $R_6$, $R_7$, and $R_8$ cannot all be hydrogen and when $R_{10}$ is absent, $R_5$, $R_6$, $R_7$, and $R_8$ cannot all be hydrogen when either $R_1$, $R_2$, $R_3$, or $R_4$ is hydroxy, or R2 is carboethoxy; or a pharmaceutically acceptable salt thereof.

The present invention further provides a composition comprising the compound described above in an amount effective to modulate cellular expression of a mammalian gene encoding erythropoietin and a carrier.

The present invention also provides a method of modulating expression of a mammalian gene encoding erythropoietin which comprises contacting a cell capable of expressing the gene with a compound having the structure:

wherein each of $R_1$, $R_2$, $R_3$, $R_4$, $R_5$, $R_6$, $R_7$ and $R_8$ may independently be hydrogen, halogen, nitro, $CF_3$, hydroxy, $C_{1-5}$ alkyl, aryl or $OR_9$, wherein $R_9$ is $C_{1-5}$ alkyl, wherein $R_{10}$ is hydrogen or $COC_{1-5}$ alkyl; or wherein any two consecutive R groups may be members of a $C_5-C_6$ membered ring, and wherein the intracyclic-dashed line represents a covalent bond which may be present or absent, with the proviso that when $R_{10}$ is present, the exocyclic-covalent bond is absent, and when $R_{10}$ is absent, the exocyclic-covalent bond is present, and with the proviso that when $R_{10}$ is absent, $R_1$, $R_2$, $R_3$, $R_4$, $R_5$, $R_6$, $R_7$, and $R_8$ cannot all be hydrogen and when $R_{10}$ is absent, $R_5$, $R_6$, $R_7$, and $R_8$ cannot all be hydrogen when either $R_1$, $R_2$, $R_3$, or $R_4$ is hydroxy, or R2 is carboethoxy; or a pharmaceutically acceptable salt thereof, and wherein the compound is in an amount effective to modulate the expression of the gene.

The present invention also provides a method for treating a subject having an erythropoietin deficiency which comprises administering to the subject an amount of a compound effective to treat the subject, wherein the compound has the structure:
wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl, wherein $R_{10}$ is hydrogen or $COC_{1-5}$ alkyl; or wherein any two consecutive R groups may be members of a $C_5-C_6$ membered ring, and wherein the intracyclic-dashed line represents a covalent bond which may be present or absent, with the proviso that when $R_{10}$ is present, the exocyclic-covalent bond is absent, and when $R_{10}$ is absent, the exocyclic-covalent bond is present, and with the proviso that when $R_{10}$ is absent, $R_1$, $R_2$, $R_3$, $R_4$, $R_5$, $R_6$, $R_7$, and $R_8$ cannot all be hydrogen and when $R_{10}$ is absent, $R_5$, $R_6$, $R_7$, and $R_8$ cannot all be hydrogen when either $R_1$, $R_2$, $R_3$, or $R_4$ is hydroxy, or $R_2$ is carboethoxy.

BRIEF DESCRIPTION OF THE FIGURES

FIGS. 1A–1B.

DETAILED DESCRIPTION OF THE INVENTION

The present invention provides a compound in substantially pure form having the structure:

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein $R_{10}$ when present is hydrogen or $COC_{1-5}$ alkyl; wherein the exocyclic-dashed line represents a covalent bond which may be present or absent, with the proviso that when $R_{10}$ is present, the exocyclic-covalent bond is absent, and when $R_{10}$ is absent, the exocyclic-covalent bond is present, and with the proviso that when $R_{10}$ is absent, $R_1$, $R_2$, $R_3$, $R_4$, $R_5$, $R_6$, $R_7$, and $R_8$ cannot all be hydrogen and when $R_{10}$ is absent, $R_5$, $R_6$, $R_7$, and $R_8$ cannot all be hydrogen when either $R_1$, $R_2$, $R_3$, or $R_4$ is hydroxy, or $R_2$ is carboethoxy.

In one embodiment, $R_2$ and $R_4$ are each methyl and $R_1$, $R_3$, $R_5$, $R_6$, $R_7$, $R_8$, and $R_{10}$ are each hydrogen, and the intracyclic covalent bond is present.

In another embodiment, $R_2$ and $R_4$ are each methyl and $R_1$, $R_3$, $R_5$, $R_6$, $R_7$ and $R_8$ are each hydrogen, $R_{10}$ is absent and the intracyclic covalent bond is present.

In a further embodiment, $R_2$ and $R_4$ are each methyl, $R_1$, $R_3$, $R_5$, $R_6$, $R_7$, $R_8$ and $R_{10}$ are each hydrogen, and the intracyclic covalent bond is absent.

The present invention also provides a compound in substantially pure form having the structure:

wherein each of $R_1$, $R_2$, $R_3$, $R_4$, $R_5$, $R_6$, $R_7$, and $R_8$ may independently be hydrogen, halogen, nitro, $CF_3$, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond is absent, and when $R_{10}$ is absent, the exocyclic-covalent bond is present.

The present invention further provides a compound in substantially pure form having the structure:

wherein each of $R_1$, $R_2$, $R_3$, and $R_4$ may independently be hydrogen, halogen, nitro, $CF_3$, $C_{1-5}$ alkyl, aryl or $OR_9$, wherein each of $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond is absent, and when $R_{10}$ is absent, the exocyclic-covalent bond is present.

The present invention also provides a compound in substantially pure form having the structure:

wherein each of $R_1$, $R_2$, $R_3$, and $R_4$ may independently be hydrogen, halogen, nitro, $CF_3$, hydroxy, $C_{1-5}$ alkyl, aryl or $OR_9$ provided that at least two of $R_1$, $R_2$, $R_3$ and $R_4$ are hydroxy, wherein each of $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond is absent, and when $R_{10}$ is absent, the exocyclic-covalent bond is present.

One embodiment of the present invention is a composition comprising such compound described herein in an amount effective to modulate cellular expression of a mammalian gene encoding erythropoietin and a carrier.

For the purposes of this invention the term halogen refers to chlorine, bromine, iodine and fluorine.

In the present invention aryl includes phenyl, benzyl, benzoyl, or naphthyl. For the purposes of this invention the aryl may be substituted or unsubstituted. Examples of suitable substituents include, but are not limited to $C_{1-5}$ alkyl, $C_{1-5}$ alkoxy, $C_{1-5}$ alkylthio, halo, nitro, cyano, hydroxy, and amino.

In one embodiment of the present invention, $R_2$ and $R_4$ are each methyl and $R_1$, $R_3$, $R_5$, $R_6$, $R_7$, $R_8$, and $R_{10}$ are each hydrogen, and the intracyclic covalent bond is present.

In another embodiment of the present invention, $R_2$ and $R_4$ are each methyl, $R_1$, $R_3$, $R_5$, $R_6$, $R_7$ and $R_8$ are each hydrogen, $R_{10}$ is absent and the intracyclic covalent bond is present.

In yet another embodiment of the present invention, $R_2$ and $R_4$ are each methyl, $R_1$, $R_3$, $R_5$, $R_6$, $R_7$, $R_8$ and $R_{10}$ are each hydrogen, and the intracyclic covalent bond is absent.

In a further embodiment of the present invention, any two consecutive R groups may be members of a $C_5$–$C_6$ membered ring. Examples of such compounds include, but are not limited to:

The compounds of the present invention are at least 80% pure, preferably at least 90% pure, and most preferably at least 95% pure.

The compounds of the present invention may be present as enantiomers, diastereoisomers or isomers, or two or more of the compounds may be present to form a racemic mixture.

The invention further provides for the (+) enantiomer of any of the compounds described herein which is a cis isomer or trans isomer. The invention also provides for the (–) enantiomer of any of the compounds described herein which is a cis isomer or a trans isomer.

The present invention also provides a method of modulating expression of a mammalian gene encoding erythropoietin which comprises contacting a cell capable of expressing the gene with a compound having the structure:

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond is absent, and when $R_{10}$ is absent, the exocyclic-covalent bond is present; and wherein the compound is in an amount effective to modulate the expression of the gene.

Examples of cells which are capable of expressing the mammalian gene which encodes erythropoietin, include but are not limited to, mammalian cells, animal cells, human cells, erythroleukemic cell lines, bone marrow cells, astrocytes (rat cells), human liver cells and human kidney cells.

In one embodiment of the present invention the cell is a human cell. In another embodiment of the present invention the cell is a human liver cell. In a further embodiment of the present invention the cell is a human kidney cell.

In one embodiment, $R_2$ and $R_4$ are each methyl and $R_1$, $R_3$, $R_5$, $R_6$, $R_7$, $R_8$, and $R_{10}$ are each hydrogen, and the intracyclic covalent bond is present.

In another embodiment, $R_2$ and $R_4$ are each methyl, $R_1$, $R_3$, $R_5$, $R_6$, $R_7$ and $R_8$ are each hydrogen, $R_{10}$ is absent, and the intracyclic covalent bond is present.

In a further embodiment, $R_2$ and $R_4$ are each methyl, $R_1$, $R_3$, $R_5$, $R_6$, $R_7$, $R_8$ and $R_{10}$ are each hydrogen, and the intracyclic covalent bond is absent.

The present invention also provides a method for treating a subject having an erythropoietin deficiency which comprises administering to the subject an amount of a compound effective to treat the subject, wherein the compound has the structure:

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond is absent, and when $R_{10}$ is absent, the exocyclic-covalent bond is present.

For the purposes of the present invention, an erythropoietin deficiency shall refer to those conditions in which a subject exhibits either a below normal hematocrit and a below normal level of Epo, or a below normal hematocrit and an average level of Epo. In one embodiment the subject's level of Epo is 90% below the average Epo level. In another embodiment of the present invention the subject's level of Epo is 40% below the average Epo level. In another embodiment of the present invention the subject's level of Epo is 10% below the average Epo level. The level of Epo in blood can be measured by any person skilled in the art, using standard methods with commercially available Epo-Elisa kits. An example of a commercially available Epo-Elisa kit is R&D Systems ELISA kit (catalogue # DEP00, Minneapolis, Minn.).

In one embodiment of the present invention the erythropoietin deficiency is associated with anemia. In another embodiment of the present invention the erythropoietin deficiency is associated with anemia due to chronic renal failure. In a further embodiment of the present invention the erythropoietin deficiency is associated with anemia due to an AZT-treated HIV-infection.

Examples of other deficiencies associated with anemia include, but are not limited to, anemia due to prematurity, anemia due to autologous blood donation, anemia due to chronic infection, anemia due to rheumatoid arthritis, anemia due to AIDS, anemia due to malignancies, anemia associated with stem cell therapy, anemia associated with irritable-bowel disease, anemia of hypothyroidism, anemia of malnutrition, anemia associated with chemotherapy and anemia associated with bone marrow transplantation.

In one embodiment of the present invention the subject is a human. In another embodiment of the present invention the subject is an animal.

The administering of the compound to the subject may be effected by any of the known methods of administration. Such methods include, but are not limited to, topical administration, parenteral administration, oral administration, or intraperitoneal, intravenous, intrathecal, intratracheal, intramuscular, or subcutaneous injection. Administration of the compound may be effected continuously or intermittently. Furthermore, the compound may be administered by itself or in combination with lipids or other carriers.

In one embodiment of the present invention the compounds described herein are administered intravenously. In another embodiment of the present invention the compounds described herein are administered intramuscularly. In a further embodiment of the present invention the compounds described herein are administered orally.

An "effective amount" as used herein refers to that amount which is effective to bring about the desired effect in the subject. Accordingly, an effective amount will depend on various factors known to those of ordinary skill in the art. Such factors include, but are not limited to, the size of the subject and the degree to which the disease from which the subject suffers has progressed. The effective amount will also depend on whether the compound is going to be administered to the subject in a single dosage or periodically over a stretch of time.

Dose ranges for topical use include, but are not limited to, 1 ng to 10 mg per dose, preferably, 10 ng to 100 $\mu$g per dose or more preferably 50 ng to 20 $\mu$g per dose. However, the administration may also be systemic. Dose ranges for systemic application include 10 ng to 50 mg/kg subject weight/day, preferably 100 ng to 10 mg/kg subject weight/day, or more preferably 1 $\mu$g to 2 mg/kg subject weight/day.

The present invention further provides a pharmaceutical composition comprising an effective compound of the compounds herein and a pharmaceutically acceptable carrier. Examples of suitable pharmaceutical carriers include any of the standard pharmaceutically accepted carriers known to those of ordinary skill in the art. Examples of such pharmaceutical carriers include, but are not limited to, phosphate buffered saline solution, water, emulsions such as oil/water emulsions or a triglyceride emulsion, various types of wetting agents, complexing agents, tablets, coated tablets and capsules. A suitable pharmaceutically acceptable carrier may be selected taking into account the chosen mode of administration.

Besides containing an effective amount of the compounds described herein the pharmaceutical compositions may also include suitable diluents, preservatives, solubilizers, emulsifiers, adjuvant and/or carriers useful for erythropoietin therapy.

The resulting pharmaceutical compositions may be liquids or lyophilized or otherwise dried formulations. Examples of suitable diluents include, but are not limited to, cosolvents, Tris-HCL, Tris-acetate and Tris-phosphate. The diluents employed may vary in their buffer content, pH and/or ionic strength. Examples of representative additives which may be used in the present invention include, but are not limited to, albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the protein, or incorporation of the material into or onto particulate preparation of polymeric compounds such as polyacetic acid, polyglycolic acid, polyvinyl pyrrolidone, etc. or into liposomes, microemulsions, micelles, unilamellar or multimellar vesicles, erythrocyte ghosts, or spheroplasts. Such compositions will influence the physical state, solubility, stability, rate of in vivo release, and rate of in vivo clearance of the compounds.

Examples of optional ingredients which may be included in the pharmaceutical compositions of the present invention include antioxidants, e.g., ascorbic acid; low molecular weight (less than about ten residues) polypeptides, i.e., polyarginine or tripeptide; proteins, such as serum albumin, gelatin, or immunoglobulins; amino acids, such as glycine, glutamic acid, aspartic acid, or arginine; chelating agents such as EDTA; and sugar alcohols such as mannitol or sorbitol.

The choice of composition will depend on the physical and chemical properties of the compounds. Controlled or sustained release compositions include formulation of lipophilic depots (e.g., fatty acids, waxes, oils). Also comprehended by the invention are particulate compositions coated with polymers (e.g., poloxamers or poloxamines) and compounds coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary nasal and oral.

Suitable topical formulations include gels, creams, solutions, emulsions, carbohydrate polymers, biodegradable matrices thereof; vapors, mists, aerosols, or other inhalants. The compounds of the present invention may be encapsulated in a wafer, wax, film or solid carrier, including chewing gums. Permeation enhancers to aid in transport to movement across the epithelial layer are also known in the art and include, but are not limited to, dimethyl sulfoxide and glycols.

This invention further provides for the hydrates and polymorphs of all of the compounds described herein.

The present invention also provides a method of preparing the compounds described herein which comprises:

(A) treating a substituted salicyclic acid methyl ester with dimethyl sulfoxide to produce a methylsulfinyl-acetophenone; and (B) condensing the methylsulfinyl-acetophenone with a substituted o-phthalaldehyde under appropriate conditions to produce the compounds of the present invention.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Throughout this section one preferred compound having the following structure is identified as Compound 1:

Compound 1

Another preferred compound has the following structure and is identified as Compound 2:

Compound 2

Another preferred compound has the following structure and is identified as Compound 3.

Compound 3

General Methods for Preparation of Compounds 1–8

The preferred compounds 1–8, are prepared according to methods outlined in Scheme 1.

Compounds of the type given for Structure I are prepared as shown in Scheme 1.

An appropriately substituted salicylic acid methyl ester (II) is treated with dimethyl sulfoxide under strong basic conditions at 60–80° C. to yield a methylsulfinyl-acetophenone (III); this is condensed with an appropriately substituted o-phthalaldehyde (IV) under basic conditions at 100–120° C. Compounds wherein the exocyclic dashed line is present, and $R_{10}$ is absent may be prepared by treatment of the compound where $R_{10}$ is hydrogen (VI) to oxidizing conditions, which may occur in situ. Compounds of the type where $R_{10}$ is $COC_{1-5}$ alkyl may be prepared by reaction of the compound where $R_{10}$ is H with an appropriate acid chloride in the presence of base at ambient temperature. Compounds wherein the cyclic dashed line is absent and $R_{10}$ is hydrogen are prepared by treatment of the sulfoxide intermediate V with a suitable reducing agent such as Raney nickel at ambient temperature.

Preparation of 3,5-dimethyl salicylic acid methyl ester (intermediate IIa):

The preferred compounds exemplified here are derived from the salicylic acid methyl ester (II, Scheme 1), wherein $R_2$ and $R_4$ are methyl. The 3,5-dimethyl salicylic acid methyl ester is prepared from the 3,5-dimethyl salicylic acid; a description of the preparation of those intermediates follows.

The 3,5-dimethylsalicylic acid is readily prepared from 2,4-dimethyl phenol and carbon dioxide: A solution of 2,4-dimethylphenol (46.55 g, 0.382 mol) in DMF (70 ml) was added to a stirred suspension of sodium hydride (60%, 17.3 g, 0.432 mol) in DMF (150 ml) over 0.75 h and stirred at 120° C. for 1.6 h. A stream of carbon dioxide was bubbled through the mixture at the same temperature for 2.3 h. The mixture was cooled to room temperature, poured onto water (600 ml) and washed with ethyl acetate (2×350 ml). The aqueous layer was treated with concentrated hydrochloric acid (90 ml) and extracted with ethyl acetate (3×400 ml). The extracts were combined, dried over magnesium sulfate and the solvent was evaporated in vacuo to give a brown oil which crystallized on standing. Yield 39.388 g, 0.237 mol, 62%.

Furthermore, the 3,5-dimethyl salicylic acid methyl ester intermediate is prepared from 3,5-dimethylsalicylic acid: A solution of 3,5-dimethylsalicylic acid (39 g) in methanol (600 ml) containing concentrated sulfuric acid (50 ml) was heated at reflux for 15 h. More concentrated sulfuric acid (25 ml) was added and the mixture was heated at reflux for 5 h. The acid was neutralized with strong aqueous sodium hydroxide and the methanol was evaporated. The residue was partitioned between saturated aqueous sodium hydrogen carbonate (500 ml) and ethyl acetate (2×500 ml). The extracts were combined, dried over magnesium sulfate and the solvent was evaporated in vacuo to give a brown solid which was recrystallized from ethanol. Yield 13.699 g, 0.076 mol, 33%.

Preparation of 3',5'-dimethyl-2'-hydroxy-2-(methysulfinyl) acetophenone (intermediate IIIa):

The 3',5'-dimethyl-2'-hydroxy-2-(methysulfinyl) acetophenone was then prepared from dimethyl sulfoxide (DMSO) and 3,5-dimethylsalicylic acid methyl ester: DMSO (250 ml) was added to sodium hydride (60%, 9.1 g, 0.228 mol). The mixture was heated at 80–90° C. for 50 minutes and then cooled to room temperature. Methyl 3,5-dimethylsalicylate (13.65 g, 75.8 mmol) was added and the mixture was stirred at 60–65° C. for 1 h. The DMSO was evaporated. The residue was dissolved in water (300 ml), adjusted to pH 5.5 with concentrated hydrochloric acid and extracted with dichloromethane (4×200 ml). The extracts were combined, dried over magnesium sulfate and the solvent was evaporated in vacuo to give a yellow solid. This was triturated with petrol (3×50 ml) and dried in vacuo. The title compound was obtained as a yellow crystalline solid. Yield 16.1 g, 71.2 mmol, 94%. Proton nmr, $\delta_H$: $d_6$-DMSO (DMSO=2.50 ppm),2.16(s, 3H, Me),2.26 (s, 3H, Me), 2.72 (s, 3H, SOMe),4.64 (ABq, 2H, $CH_2SO$), 7.33(s, 1H, Ar-H), 7.66(s, 1H, Ar-H), 11.94(s, 1H, OH). $^{13}C$ nmr: $d_6$-DMSO (DMSO=40.0 ppm), 15.5 (Me), 20.4 (Me), 39.2 ($CH_2$), 62.2 (SOMe)119.2, 126.6, 127.9, 129.6, 139.6, 158.4 (Ar), 199.9 (CO).

EXAMPLE 1: Preparation of Compound 1

A suspension of 3',5'-dimethyl-2'-hydroxy-2-(methysulfinyl)acetophenone (0.502 g, 2.2 mmol) and benzene-1,2-dicarboxaldehyde (0.227 g, 2.1 mmol) in butanol containing 0.2% v/v piperidine (16 ml) was heated at 110° C. After 10 minutes a solution formed. After 2 h more benzene-1,2-dicarboxaldehyde (0.195 g, 1.5 mmol) was added. After a further hour the mixture was cooled on an ice bath. The resulting light orange solid was collected by filtration. The filter cake was washed with ether (20 ml) and the solid was dried under vacuum to give the title compound as a pale orange crystalline solid. Yield 0.32 g, 1.15 mmol, 52%. Compound 1 was characterized by the following properties:

Proton nmr, $\delta_H$: $d_6$-DMSO 2.40(s, 3H, Me), 2.55 (s, 3H, Me), 5.57, (d, 1H, J=7.9 Hz, CHOH), 5.79 (d, 1H, J=7.9 Hz CHOH), 7.48–7.83 (overlapping m, 6H, Ar-H)

the EI mass spectrum gave, m/z=278 ($M^+$): 262, 250, ((M-CO)$^+$). TLC: $SiO_2$, ether/acetic acid (120:1 v/v), Rf=0.84.

EXAMPLE 2: Preparation of Compound 2

A suspension of Compound 1 (2.0 g, 7.2 mmol) and acetic anhydride (41 ml) in DMSO (315 ml) was heated at 50° C. under argon. After 24h the reaction mixture was diluted with water (600 ml), filtered and the residue was washed with water (50 ml) and dried at room temperature in vacuo. Yield 1.9 g, 6.9 mmol, 96%. The EI mass spectrum gave m/z=276 ($M^+$) and 248 ((M-CO)+). TLC: $SiO_2$ and ethyl acetate/triethylamine (96:5 v/v), Rf=0.60. Proton nmr, $\delta_H$: $d_6$-DMSO 2.41 (s, 3H, Me), 2.58 (s, 3H, Me), 7.56 (m, 1H, Ar-H), 7.68–7.78 (m, 4H, Ar-H), 7.90 (m, 1H, Ar-H).

EXAMPLE 3: Preparation of Compound 3

A suspension of 3',5'-dimethyl-2'-(methylsulfinyl) acetophenone (3.36 g, 14.9 mmol) and benzene-1,2-dicarboxaldehyde (0.991 g, 14.9 mmol) in butanol containing 0.2% v/v piperidine (113 ml) was heated below the boiling point of the solvent. After 2.5 h heating was stopped and the reaction mixture was allowed to cool to room temperature. An orange precipitate, which was identified as Compound 1 was isolated by filtration and washed with ether. The combined filtrate and washings were evaporated in vacuo until a second precipitate began to form whereupon the mixture was set aside at 0° C. After 16 h the sulfoxide (see structure V, $R_2$, $R_4$=methyl, $R_1$, $R_3$, $R_5$, $R_6$, $R_7$, $R_8$=H in Scheme 1) was isolated as a white precipitate. The melting range was 308–311° C. (corrected). TLC: $SiO_2$, (ethyl acetate), Rf=0.28. FAB+ mass spectrum gave m/z=365 (M+Na) and 343 (M+H).

Raney nickel (2.3 g of a 50% slurry in water) was added to a solution of V (0.102 g), 0.30 mmol) in THF (20 ml) and the reaction was stirred at room temperature. After 16 h the reaction mixture was filtered through celite and the residue was washed with THF (10 ml) and methanol (10 ml). The combined filtrate and washing were evaporated in vacuo and purified by flash column chromatography ($SiO_2$, $CH_2Cl_2$, (100 ml), $CH_2Cl_2$/MeOH 50:1 v/v (100 ml), $CH_2Cl_2$/MEOH, 25:1 v/v (100 mL). Fractions containing the required product were combined and purified further by preparative TLC solvent system $CH_2Cl_2$/MeOH 25:1 v/v) to furnish Compound 3 as a white solid (0.046 g, 0.16 mmol, 55%). The melting range was 202.3–206.3° C. (corrected). TLC: $SiO_2$ and $CH_2Cl_2$/methanol (50:1 v/v) ,Rf=0.21. FAB+ mass spectrometry gave m/z=280 ($M^+$) and 262 ($M-H_2O$).

Additional Preferred Examples:

Compound 4

Compound 5

Compound 6

Compound 7

Compound 8

Compound 9

Compound 10

-continued

Compound 11

EXAMPLE 4: Preparation of Compound 4

Acetyl chloride (0.3 ml, 0.0042 mol) was added to a suspension of Compound 1 (0.179 g, 0.00064 mol) in dichloromethane (15 ml) containing diisopropylethylamine (0.2 ml, 0.0011 mol) and dimethylaminopyridine (0.009 g, 0.00007 mol) and the mixture was stirred at ambient temperature. After 2 days the reaction mixture was diluted with dichloromethane (20 ml) and washed with hydrochloric acid (2×30 ml of a 1M solution), water (30 ml) and brine (30 ml), dried over magnesium sulfate and evaporated in vacuo. The residue was purified by flash column chromatography ($SiO_2$, ethyl acetate/petroleum ether (60–80° C.) to furnish Compound 4 as a white crystalline solid. Yield 0.159 g, 0.0005 mol 77%.

Compound 4 was characterized by the following properties:

TLC: $SiO_2$ and ethyl acetate/petroleum ether (60–80° C.) (1:1 v/v), $R_f$=0.37.

Proton nmr, $\delta_H$ DMSO 2.14 (s, 3H, MeCO), 2.41 (s, 3H, Me), 2.57 (s, 3H, Me), 6.85 (s, 1H, CH), 7.54 (broad s, 1H, Ar-H), 7.59–7.65 (overlapping m, 3H, Ar-H), 7.73 (broad s, 1H, Ar-H), 7.90 (m, 1H, Ar-H).

EXAMPLE 5: Preparation of Compounds 5 and 6

A suspension of 3',5'-dimethyl-2'-hydroxy-2-(methylsulfinyl)acetophenone (0.38 g, 0.0017 mol) and 4-chlorobenzene-1,2-dicarboxaldehyde (0.32 g, 0.0019 mol) in toluene containing 0.2% v/v piperidine (10 ml) was heated to 105° C. under argon. After 2 h the mixture was cooled to ambient temperature and a 1:1 mixture of Compounds 5 and 6 was collected as a yellow solid. Yield 0.070 g, 0.00022 mol, 13%.

The mixture of Compounds 5 and 6 was characterized by the following properties:

the FAB+ mass spectrum gave, m/z=313/315 ($M^+$) Proton nmr, $\delta_H$DMSO 2.41 (s, 3H, Me, both isomers), 2.52 (s, 3H, Me, one isomer), 2.53 (s, 3H, Me, one isomer), 5.50–5.57 (overlapping m, 1H, CH, both isomers), 5.88–5.94 (overlapping m, 1H, OH, both isomers), 7.47 (broad s, 1H, Ar-H, both isomers), 7.55–7.70 (overlapping m, 2H, Ar-H, both isomers), 7.71 (broad s, 1H, Ar-H), 7.77–7.85 (overlapping m, 1H, Ar-H, both isomers)

EXAMPLE 6: Preparation of Compounds 7 and 8

A suspension of 3',5'-dimethyl-2'-hydroxy-2-(methylsulfinyl)acetophenone (0.66 g, 0.0029 mol) and 4-fluorobenzene-1,2-dicarboxaldehyde (0.49 g, 0.0032 mol) in toluene containing 0.2% v/v piperidine (20 ml) was heated to 105° C. under argon. After 2 h the mixture was cooled to ambient temperature and a 1:1 mixture of Compounds 7 and 8 was collected as an orange solid. Yield 0.155 g, 0.00052 mol, 18%.

The mixture of Compounds 7 and 8 was characterized by the following properties:

the EI+ mass spectrum gave, m/z=296 (M+) Proton nmr, $\delta_H$ DMSO 2.37 (s, 3H, Me, both isomers), 2.51 (s, 3H, Me, one isomer), 2.52 (s, 3H, Me, one isomer), 5.49 (d, 1H, CH, one isomer), 5.52 (d, 1H, CH, one isomer), 5.85 (d, 1H, OH, one isomer), 5.93 (d, 1H, OH, one isomer), 7.35 (m, 1H, Ar-H, both isomers), 7.46 (broad s, 1H, Ar-H, both isomers) 7.47 (m, 1H, Ar-H, one isomer) 7.64 (m, 1H, Ar-H, both isomers), 7.70 (broad s, 1H, Ar-H, both isomers) 7.81 (m, 1H, Ar-H, one isomer)

EXAMPLE 7: Preparation of Compounds 9 and 10

A suspension of 3',5'-dimethyl-2'-hydroxy-2-(methylsulfinyl)acetophenone (0.330 g, 0.0015 mol) and 3-fluorobenzene-1,2-dicarboxaldehyde (0.176 g, 0.0012 mol) in toluene containing 0.2% v/v piperidine (5 ml) was heated to 125° C. under argon. After 3 hours the mixture was cooled to ambient temperature and a precipitate was collected which was purified by flash column chromatography (SiO$_2$, dichloromethane/methanol, 50:1 v/v) to furnish an approximately 3:2 mixture of Compounds 9 and 10 as a yellow solid in which the assignment of major and minor components was not determined. Yield 0.006 g, 0.00002 mol, 1.4%)

The mixture of Compounds 9 and 10 was characterized by the following properties:

the positive electrospray mass spectrum gave, m/z=297 (M+H)+

Proton nmr, $\delta_H$ CDCl$_3$ 2.46 (s, 3H, Me, both isomers), 2.58 (s, 3H, Me, one isomer), 5.87 (s, 1H, CH, minor isomer), 6.09 s, 1H, CH, major isomer), 7.15–7.25 (m, 1H, Ar-H, both isomers), 7.38 (m, 1H, Ar-H, both isomers), 7.46–7.60 (overlapping m, 2H, Ar-H, both isomer), 7.92 (m, 1H, Ar-H, minor isomer), 7.93 (m, 1H, Ar-H, major isomer)

EXAMPLE 8: Preparation of Compound 11

A suspension of 3',5'-dimethyl-2'-hydroxy-2-(methylsulfinyl)acetophenone (0.340 g, 0.0015 mol) and 3-fluorobenzene-1,2-dicarboxaldehyde (0.500 g, 0.0017 mol) in toluene containing 0.2% v/v piperidine (6 ml) was heated to 105° C. under argon. After 6 hours the mixture was cooled to ambient temperature and Compound 11 was collected as an orange precipitate. Yield 0.097 g, 0.0002 mol, 15%. Compound 11 was characterized by the following properties: the positive APCI mass spectrum gave, m/z=433/435/437 (M+H)+

Proton nmr, $\delta_H$ CDCl$_3$ 2.44 (s, 3H, Me), 2.60 (s, 3H, Me), 7.40 (broad s, 1H, Ar-H), 7.93 (s, 1H, Ar-H), 7.97 (s, broad s, 2H, Ar-H).

Biological Assays and Epo Induction

The effects of compounds on the expression of the human Epo gene in the human liver cell-line, Hep3B, was determined by both amplification of the mRNA by rt-PCR and by measurement of the secreted epo protein by an ELISA.

An R&D Systems ELISA kit (catalogue # DEP00) was used to determine the effects of the compounds on secretion of the native epo following the manufacturer's protocol. For this assay cells were plated at 200,000 cells/well in a 24 well tissue culture dish in DMEM medium supplemented with 10%-fetal calf serum (fcs), 1-glutamine, and penicillin/streptomycin. After a recovery period of 24 hours the medium was replaced with 500 μl fresh medium and test compound was added in DMSO to give a final concentration of 0.5% DMSO. Epo secretion was measured 8–48 hours after compound addition and compared to the level measured in the cells treated with compound vehicle alone, i.e. DMSO. The optical density (OD) value is directly and specifically proportional to the amount of epo secreted by the cells. Compound 1 was shown to induce EPO secretion in Hep3B cells at low nanomolar concentrations. The results for Compound 1 are summarized in Table 1.

TABLE 1

Response of the epo ELISA assay to Hep3B cultures treated with vehicle (DMSO), positive control (CoCl$_2$), and Compound 1.

| Sample | Concentration | Expt 1 (G51) (OD units - ELISA) | Expt 2 (G49) (OD units - ELISA) |
|---|---|---|---|
| 8 hrs | | | |
| DMSO | 0.5% | 0.010 | 0.055 |
| CoCl$_2$ | 20 μM | 0.166 | 0.211 |
| Compound 1 | 20 μM | 0.489 | 0.537 |
| Compound 1 | 1 μM | 0.509 | 0.555 |
| Compound 1 | 50 nM | 0.494 | 0.534 |
| Compound 1 | 2.5 nM | 0.496 | 0.443 |
| Compound 1 | 125 pM | 0.448 | 0.220 |
| Compound 1 | 6.25 pM | 0.426 | 0.017 |
| 24 hrs | | | |
| DMSO | 0.5% | 0.089 | 0.130 |
| CoCl$_2$ | 20 μM | 0.243 | 1.197 |
| Compound 1 | 20 μM | 0.575 | 0.498 |
| Compound 1 | 1 μM | 0.621 | 0.594 |
| Compound 1 | 50 nM | 0.548 | 0.650 |
| Compound 1 | 2.5 nM | 0.532 | 0.468 |
| Compound 1 | 125 pM | 0.450 | 0.266 |
| Compound 1 | 6.25 pM | 0.505 | 0.111 |

Figure 1A:
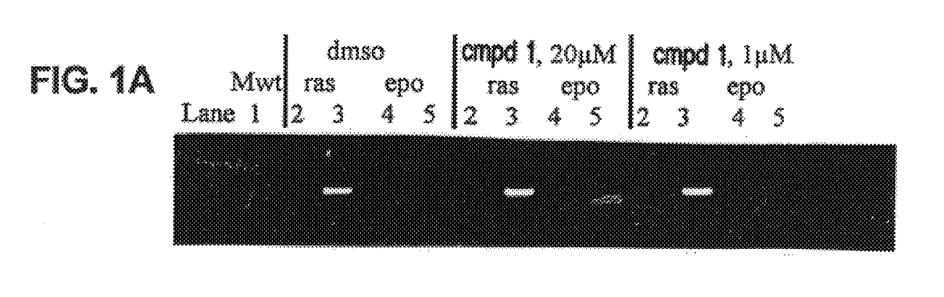
FIGS. 1A and 1B illustrate the results of rt-pcr of mRNA from Hep3B cells treated with compound 1 at 20 μM, 1 μM, 50 nM, 2.5 nM or 0.125 nM. Lane 1 contains a DNA mass ladder to indicate molecular weights, lanes 2–5 contain the products for k-ras (lanes 2 and 3) and epo(lanes 4 and 5) amplified from cells treated with DMSO or compound 1. Lanes 2 and 4 are the product generated from 1 μl of cDNA template and lanes 3 and 5 are from 5 μl cDNA template. There is no difference in the intensity of the k-ras band between control and treated samples. However, an epo transcript is only evident in the cells treated with compound 1; intensity of the epo band increases with increasing concentration of compound 1.
Figure 1B:
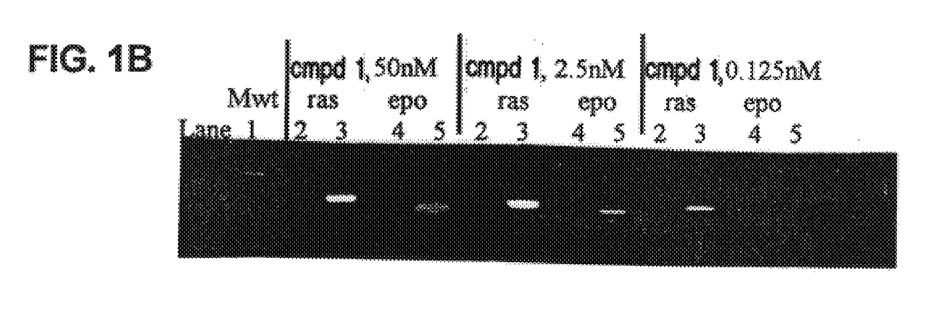

To demonstrate that the increase in secretion of Epo was due to increased transcription of the Epo gene, RT-PCR was used to detect Epo transcript (RNA) in Hep3B cells treated with the test compounds (as above). Total RNA was isolated from the cells using Micro-Perfect RNA kit from 5-Prime-3-Prime, Inc. (catalogue number 2-036364) according to the manufacturers instructions. For these experiments cells were plated at 500,000 to 1,000,000 cells per well in a 6-well plate containing DMEM medium supplemented with 10% fcs, 1-glutamine, and penicillin/streptomycin. After a 24 hour recovery period the cells were treated with test compound (added in DMSO). Total RNA was isolated between 2 and 24 hours after compound addition. Complementary DNA was prepared from 2 μg of total RNA by annealing random hexamer primers at 70° C. for 5 minutes followed by synthesis of the complementary strand of DNA for one hour at 42° C. with avian reverse transcriptase. An aliquot of the cDNA was then amplified in 40 cycles of the polymerase chain reaction using primers for both K-ras and Epo. The products of the reaction were visualized on a 2% agarose gel stained with ethidium bromide. In the absence of inducing agent, DNA bands corresponding to Epo message were not detected. FIG. 1 illustrates the results of rt-pcr of mRNA from Hep3B cells treated with compound 1 at 20 μM, 1 μM, 50 nM, 2.5 nM or 125 pM. Lane 1 contains a DNA mass ladder to indicate molecular weights, lanes 2–5 contain the products for k-ras (lanes 2 and 3) and epo (lanes 4 and 5) amplified from cells treated with DMSO or compound 1. Lanes 2 and 4 are the product generated from 1 μl of cDNA template and lanes 3 and 5 are from 5 μl cDNA template; in this experiment, only product from 5 μl cDNA is detectable. Compound 1 and dmso have no influence on expression of the k-ras gene; the same amount of k-ras product is detected in cells treated with compound 1 and DMSO. However, an epo transcript is only evident in the cells treated with compound 1; intensity of the epo band increases with increasing concentration of compound 1.

EXAMPLE

Patient is presented with anemia, is transfusion dependent, and has an hematocrit of 20%. Compound is given orally, at a dose of 1 mg/kg daily over a period of several weeks. The effect of the compound is monitored by measuring the hematocrit of the patient, once a week, over the period. Compound is effective when hematocrit rises to 30–35% and patient is no longer transfusion dependent. Dose of compound is adjusted, if needed, to maintain this hematocrit.

Patient is scheduled for vascular surgery in two months and has chosen autologous blood donation to collect several units of his own blood for the procedure. Compound is given orally, once a day, at a dose of 1 mg/kg over a three week period. Within this time, the patient visits the hospital every 3 to 4 days and his hematocrit is measured. Upon each visit, if the hematocrit is >34%, a unit of blood is donated. Compound allows patient to donate 6 units of blood.

What is claimed is:

1. A compound having the structure:

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein $R_{10}$ when present is hydrogen or $COC_{1-5}$ alkyl; wherein the exocyclic-dashed line represents a covalent bond which may be present or absent, with the proviso that when $R_{10}$ is present, the exocyclic-covalent bond represented by the exocyclic dashed bond is absent, and when $R_{10}$ is absent, the exocyclic-covalent bond represented by the exocyclic dashed bond is present, and with the proviso that when $R_{10}$ is absent, $R_1$, $R_2$, $R_3$, $R_4$, $R_5$, $R_6$, $R_7$, and $R_8$ cannot all be hydrogen and when $R_{10}$ is absent, $R_5$, $R_6$, $R_7$, and $R_8$ cannot all be hydrogen when either $R_1$, $R_2$, $R_3$, or $R_4$ is OH, or $R_2$ is $C(=O)OCH_2CH_3$.

2. The compound of claim 1, wherein $R_2$ and $R_4$ are each methyl and $R_1$, $R_3$, $R_5$, $R_6$, $R_7$, $R_8$, and $R_{10}$ are each hydrogen, and the intracyclic covalent bond represented by the intracyclic dashed bond is present.

3. The compound of claim 1, wherein $R_2$ and $R_4$ are each methyl and $R_1$, $R_3$, $R_5$, $R_6$, $R_7$ and $R_8$ are each hydrogen, $R_{10}$ is absent and the intracyclic covalent bond represented by the intracyclic dashed bond is present.

4. The compound of claim 1, wherein $R_2$ and $R_4$ are each methyl, $R_1$, $R_3$, $R_5$, $R_6$, $R_7$, $R_8$ and $R_{10}$ are each hydrogen, and the intracyclic covalent bond represented by the intracyclic dashed bond is absent.

5. A compound having the structure:

wherein each of $R_1$, $R_2$, $R_3$, $R_4$, $R_5$, $R_6$, $R_7$, and $R_8$ may independently be hydrogen, halogen, nitro, $CF_3$, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond represented by the exocyclic dashed bond is absent, and when $R_{10}$ is absent, the exocyclic-covalent bond represented by the exocyclic dashed bond is present.

6. A compound having the structure:

wherein each of $R_1$, $R_2$, $R_3$, and $R_4$ may independently be hydrogen, halogen, nitro, $CF_3$, $C_{1-5}$ alkyl, aryl or $OR_9$, wherein each of $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond represented by the exocyclic dashed bond is absent, and when $R_{10}$ is absent, the exocyclic-covalent bond represented by the exocyclic dashed bond is present.

7. A compound having the structure:

wherein each of $R_1$, $R_2$, $R_3$, and $R_4$ may independently be hydrogen, halogen, nitro, $CF_3$, hydroxy, $C_{1-5}$ alkyl, aryl or $OR_9$ provided that at least two of $R_1$, $R_2$, $R_3$ and $R_4$ are hydroxy, wherein each of $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$-$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond represented by the exocyclic dashed bond is absent, and when $R_{10}$ is absent, the exocyclic-covalent bond represented by the exocyclic dashed bond is present.

8. A composition comprising the compound of any one of claims 1, 2, 3, 4, 5, 6 or 7 in an amount effective to modulate cellular expression of a mammalian gene encoding erythropoietin and a carrier.

9. A method of modulating expression of a mammalian gene encoding erythropoietin which comprises contacting a cell capable of expressing the gene with a compound having the structure:

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond represented by the exocyclic dashed bond is absent, and when $R_{10}$ is absent, the exocyclic-covalent bond represented by the exocyclic dashed bond is present;
and wherein the compound is in an amount effective to modulate the expression of the gene.

10. The method of claim 9, wherein $R_2$ and $R_4$ are each methyl and $R_1$, $R_3$, $R_5$, $R_6$, $R_7$, $R_8$, and $R_{10}$ are each hydrogen, and the intracyclic covalent bond represented by the intracyclic dashed bond is present.

11. The method of claim 9, wherein $R_2$ and $R_4$ are each methyl, $R_1$, $R_3$, $R_5$, $R_6$, $R_7$ and $R_8$ are each hydrogen, $R_{10}$ is absent, and the intracyclic covalent bond represented by the intracyclic dashed bond is present.

12. The method of claim 9, wherein $R_2$ and $R_4$ are each methyl, $R_1$, $R_3$, $R_5$, $R_6$, $R_7$, $R_8$ and $R_{10}$ are each hydrogen, and the intracyclic covalent bond represented by the intracyclic dashed bond is absent.

13. The method of claim 9, wherein the cell is a human cell.

14. The method of claim 13, wherein the human cell is a human liver cell.

15. The method of claim 13, wherein the human cell is a human kidney cell.

16. A method for treating a subject having an erythropoietin deficiency which comprises administering to the subject an amount of a compound effective to treat the subject, wherein the compound has the structure:

wherein each of $R_1$, $R_2$, $R_3$, $R_4$, $R_5$, $R_6$, $R_7$, and $R_8$ may independently be hydrogen, halogen, nitro, $CF_3$, hydroxy, $C_{1-5}$ alkyl, aryl or $OR_9$, wherein $R_9$ is $C_{1-5}$ alkyl; or wherein any two consecutive R groups may be members of a $C_5$–$C_6$ membered ring, and wherein the intracyclic-dashed line represents a covalent bond which may be present or absent; wherein the exocyclic-dashed line represents a covalent bond which may be present or absent, with the proviso that when $R_{10}$ is hydrogen or $COC_{1-5}$ alkyl, the exocyclic-covalent bond represented by the exocyclic dashed bond is absent, and when $R_{10}$ is absent, the exocyclic-covalent bond represented by the exocyclic dashed bond is present.

17. The method of claim 16, wherein the deficiency is associated with anemia.

18. The method of claim 17, wherein the disorder is associated with anemia due to chronic renal failure.

19. The method of claim 17, wherein the deficiency is associated with anemia due to an AZT-treated HIV-infection.

20. The method of claim 16, wherein $R_2$ and $R_4$ are each methyl and $R_1$, $R_3$, $R_5$, $R_6$, $R_7$, $R_8$, and $R_{10}$ are each hydrogen, and the intracyclic covalent bond represented by the intracyclic dashed bond is present.

21. The method of claim 16, wherein $R_2$ and $R_4$ are each methyl, $R_1$, $R_3$, $R_5$, $R_6$, $R_7$ and $R_8$ are each hydrogen, $R_{10}$ is absent, and the intracyclic covalent bond represented by the intracyclic dashed bond is present.

22. The method of claim 16, wherein $R_2$ and $R_4$ are each methyl, $R_1$, $R_3$, $R_5$, $R_6$, $R_7$, $R_8$ and $R_{10}$ are each hydrogen, and the intracyclic covalent bond represented by the intracyclic dashed bond is absent.

23. The method of claim 16, wherein the subject is a human.

24. The method of claim 16, wherein the subject is an animal.

25. The method of claim 16, wherein the compound is administered intravenously.

26. The method of claim 16, wherein the compound is administered intramuscularly.

27. The method of claim 16, wherein the compound is administered orally.

28. A method of preparing the compound of claim 1 which comprises:

(A) treating a substituted salicylic acid methyl ester having the structure:

with dimethyl sulfoxide to produce a methylsulfinyl-acetophenone under basic conditions at 60–80° C. to yield a methylsulfinyl acetophenone having the structure:

and (B) reacting the methylsulfinyl-acetophenone with a substituted o-phthalaldehyde having the structure:

under basic conditions at 100–120° C. to produce the compound of claim 1.

* * * * *